US012697220B2

(12) United States Patent
Nolan et al.

(10) Patent No.:  US 12,697,220 B2
(45) Date of Patent:  Aug. 4, 2026

(54) IMPLANTABLE INFLATABLE DEVICE HAVING A FILTER

(71) Applicant: Boston Scientific Scimed, Inc., Maple Grove, MN (US)

(72) Inventors: Daragh Nolan, County Waterford (IE); Thomas Sinnott, Wexford (IE); Richard Percy, Leamlara (IE); James Michael English, Cahir (IE); Barbara Belisa Soffiati, Clonmel (IE); Brian P. Watschke, Minneapolis, MN (US); Noel Smith, Windgap (IE); Eduardo Marcos Larangeira, Cork City (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 874 days.

(21) Appl. No.: 18/068,081

(22) Filed: Dec. 19, 2022

(65) Prior Publication Data

US 2023/0190472 A1     Jun. 22, 2023

Related U.S. Application Data

(60) Provisional application No. 63/265,810, filed on Dec. 21, 2021.

(51) Int. Cl.
*A61F 2/26*        (2006.01)
*F04B 23/02*       (2006.01)
(Continued)

(52) U.S. Cl.
CPC ........ *A61F 2/26* (2013.01); *A61F 2220/0008* (2013.01)

(58) Field of Classification Search
CPC .... A61F 2/26; A61F 2220/0008; A61F 2/004; F04B 23/04; F04B 23/02; F04B 53/20
See application file for complete search history.

(56) References Cited

U.S. PATENT DOCUMENTS 4,222,377 A * 9/1980 Burton ..................... A61F 2/004
                                                        600/38
4,766,889 A * 8/1988 Trick ......................... A61F 2/26
                                                        600/40

(Continued)

FOREIGN PATENT DOCUMENTS

CA          3041321 A1 * 11/2019 ............. A61L 2/022
CN      102596104 A  *  7/2012 ......... A61B 17/8825

(Continued)

OTHER PUBLICATIONS

International Search Report and Written Opinion for PCT Application No. PCT/US2022/082041, mailed on Apr. 14, 2023, 14 pages.

(Continued)

*Primary Examiner* — Brian L Casler
(74) *Attorney, Agent, or Firm* — Brake Hughes Bellermann LLP

(57)          ABSTRACT

An implantable inflatable device includes a fluid reservoir defining a cavity, an inflatable member, a pump assembly configured to transfer fluid from the fluid reservoir to the inflatable member, and a filter member. The fluid being configured to pass through the filter member when the pump assembly transfers the fluid from the fluid reservoir to the inflatable member.

18 Claims, 9 Drawing Sheets

(51) Int. Cl.
   *F04B 23/04*      (2006.01)
   *F04B 53/20*      (2006.01)

(56)          References Cited

U.S. PATENT DOCUMENTS

| | | | |
|---|---|---|---|
| 4,900,312 A * | 2/1990 | Nadeau | A61M 39/0208 |
| | | | 604/246 |
| 5,823,991 A * | 10/1998 | Shim | A61F 5/41 |
| | | | 604/48 |
| 10,952,855 B2 | 3/2021 | Evans et al. | |
| 2004/0138523 A1 * | 7/2004 | Kuyava | A61F 2/26 |
| | | | 600/40 |
| 2012/0157759 A1 | 6/2012 | Wirbisky et al. | |
| 2017/0273792 A1 * | 9/2017 | Evans | A61F 2/26 |
| 2018/0042724 A1 * | 2/2018 | DiLoreto | A61F 2/26 |

FOREIGN PATENT DOCUMENTS

| | | | | |
|---|---|---|---|---|
| JP | 2008513182 A | 5/2008 | | |
| JP | 2019509155 A | 4/2019 | | |
| WO | WO-2010102961 A1 * | 9/2010 | | B01D 63/08 |

OTHER PUBLICATIONS

Office Action for Japanese Application No. 2024-534266 (with English translation), mailed Mar. 31, 2025, 8 pages.

\* cited by examiner

100

120

170

190

110

130

160

150

720

720

IMPLANTABLE INFLATABLE DEVICE HAVING A FILTER

CROSS-REFERENCE TO RELATED APPLICATION

This application claims priority to U.S. Provisional Patent Application No. 63/265,810, filed on Dec. 21, 2021, entitled "IMPLANTABLE INFLATABLE DEVICE HAVING A FILTER", the disclosure of which is incorporated by reference herein in its entirety.

TECHNICAL FIELD

This disclosure relates generally to bodily implants, and more specifically to bodily implants including an inflatable member, a fluid reservoir, and a pump.

BACKGROUND

Implantable inflatable devices often include one or more pumps that regulate a flow of fluid between different portions of the implantable device to provide for inflation and deflation of one or more fluid fillable implant components of the device. For example, some implantable inflatable devices include an inflatable member, a fluid reservoir, and a pump or pump assembly. In such implantable inflatable devices, it may be desirable to keep particles out of the pumps or pump assemblies. For example, it may be desirable to keep particles out of the pumps of pump assemblies to help prevent pump or valve fouling. Accordingly, there is a need for an implantable inflatable device that includes a system for keeping particles out of or away from the pumps or pump assemblies.

SUMMARY

According to an aspect, an implantable inflatable device includes a fluid reservoir defining a cavity, an inflatable member, a pump assembly configured to transfer fluid from the fluid reservoir to the inflatable member, and a filter member. The fluid being configured to pass through the filter member when the pump assembly transfers the fluid between the fluid reservoir and the inflatable member. For example, in some embodiments the fluid is configured to pass through the filter member when the pump assembly transfers fluid from the fluid reservoir to the inflatable member. In some embodiments, the fluid is configured to pass through the filter member when the pump assembly transfers fluid from the inflatable member to the fluid reservoir. In some embodiments, the fluid is configured to pass through the filter member when the pump assembly transfers fluid from the inflatable member to the fluid reservoir and when the pump assembly transfers fluid from the fluid reservoir to the inflatable member.

In some embodiments, the pump assembly includes a pump, the filter is operatively coupled between the pump and the fluid reservoir. In some embodiments, the pump assembly includes a pump, the filter is operatively coupled between the pump and the inflatable member.

In some embodiments, the inflatable device includes a connection member extending between the fluid reservoir and the pump assembly to operatively couple the fluid reservoir to the pump assembly, the filter being disposed within the connection member. In some embodiments, the inflatable device includes a connection member extending between the inflatable member and the pump assembly to operatively couple the inflatable member to the pump assembly, the filter being disposed within the connection member.

In some embodiments, the filter is a self-cleaning filter. In some embodiments, the filter defines a fluid pathway, the fluid pathway having a tapered shape. In some embodiments, the filter defines a first opening, a second opening, and a lumen extending between the first opening and the second opening, the first opening having a size, the second opening having a size, the size of the first opening being larger than the size of the second opening. In some embodiments, the filter defines a first opening, a second opening, a third opening, and fluid pathway fluidically coupling the first opening, the second opening, and the third opening.

In some embodiments, the filter defines a first opening, a second opening, a third opening, and fluid pathway fluidically coupling the first opening, the second opening, and the third opening, the first opening having a size, the second opening having a size, the third opening having a size, the size of the first opening being different than the size of the second opening and being different than the size of the third opening. In some embodiments, the filter has a first side and a second side opposite the first side, the filter defines a first opening, a second opening, a third opening, and fluid pathway fluidically coupling the first opening, the second opening, and the third opening, the first opening being disposed on the first side of the filter, the second opening being disposed on the second side of the filter, the third opening being disposed on the second side of the filter.

In some embodiments, the filter is a lattice filter. In some embodiments, the filter defines a fluid pathway, the fluid pathway having a torturous path.

In some embodiments, the filter is disposed within the pump assembly. In some embodiments, the pump assembly includes a housing, the housing having anchoring members.

In some embodiments, an implantable inflatable device includes a fluid reservoir defining a cavity, an inflatable member, a pump assembly configured to transfer fluid from the fluid reservoir to the inflatable member, a first connection member extending between the fluid reservoir and the pump assembly, a second connection member extending between the inflatable member and the pump assembly, and a filter member.

In some embodiments, the filter member is disposed within the first connection member. In some embodiments, the filter member is disposed within the second connection member. In some embodiments, the filter is a self-cleaning filter. In some embodiments, the filter defines a fluid pathway, the fluid pathway having a tapered shape.

DETAILED DESCRIPTION

Detailed implementations are disclosed herein. However, it is understood that the disclosed implementations are merely examples, which may be embodied in various forms. Therefore, specific structural and functional details disclosed herein are not to be interpreted as limiting, but merely as a basis for the claims and as a representative basis for teaching one skilled in the art to variously employ the implementations in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the implementations are directed to bodily implants. The term patient or user may hereinafter be used for a person who benefits from the medical device or the methods disclosed in the present disclosure. For example, the patient can be a person whose body is implanted with the medical device or the method disclosed for operating the medical device by the present disclosure.

Figure 1:
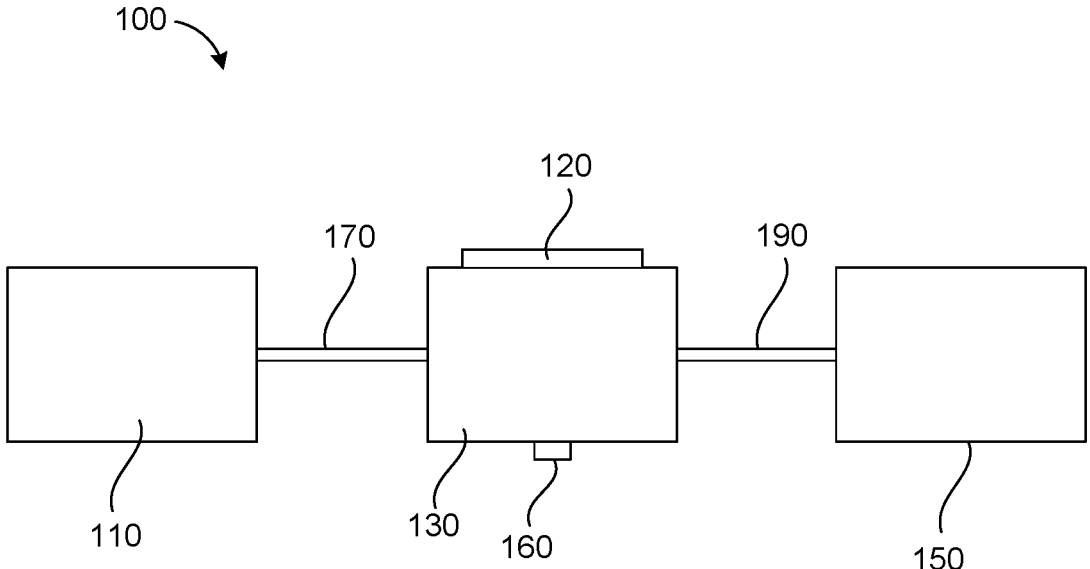
FIG. 1 is a schematic illustration of an implantable inflatable device according to an aspect.

FIG. 1 is a schematic illustration of an implantable inflatable device 100. The device 100 includes a fluid reservoir 110, a pump assembly 130, and an inflatable member 150. The fluid reservoir 110 is operatively or fluidically coupled to the pump assembly 130 via connection member 170. The connection member 170 may be a tubular member such as a kink resistant tubing (KRT). In other implementations, the fluid reservoir 110 is operatively or fluidically coupled to the pump assembly 130 via a different mechanism. Similarly, the inflatable member 150 is operatively or fluidically coupled to the pump assembly 130 via connection member 190. Connection member 190 may be a tubular member such as a kink resistant tubing (KRT). In other implementations, the inflatable member 150 is operatively or fluidically coupled to the pump assembly 130 via a different mechanism.

The implantable inflatable device 100 may be configured to be implanted into a body of a patient or user. For example, in some embodiments, the implantable inflatable device 100 is a penile implant. In such embodiments, the inflatable member 150 may be implanted into the corpus cavernosae of the patient or user, the fluid reservoir 110 may be implanted in the abdomen or pelvic cavity of the user (e.g., the fluid reservoir 110 may be implanted in the lower portion of the user's abdominal cavity or the upper portion of the user's pelvic cavity), and the pump assembly 130 may be implanted into a portion of the body of the user, such as an abdomen of the user. In other embodiments, the implantable inflatable device 100 is implanted into a different portion of the body of the patient and/or is implanted for a different purpose. For example, in some embodiments, the implantable inflatable device 100 may be an artificial sphincter, such as an artificial urinary sphincter.

The pump assembly 130 may include a pump or more than one pump that is configured pump fluid into the inflatable member 150 during an inflation cycle. In some examples, the pump or pumps maybe be manually controlled by the user or may be mechanically and/or programmatically controlled by a controller.

The inflatable member 150 may be capable of expanding upon the injection of fluid into a cavity of the inflatable member 150. For instance, upon injection of the fluid into the inflatable member 150, the inflatable member 150 may increase its length and/or width, as well as increase its rigidity. In some examples, the inflatable member 150 may include a pair of inflatable cylinders or at least two cylinders, e.g., a first cylinder member and a second cylinder member. The volumetric capacity of the inflatable member 150 may depend on the size of the inflatable cylinders.

The fluid reservoir 110 may include a container having an internal cavity or chamber configured to hold or house fluid that is used to inflate the inflatable member 150. The volumetric capacity of the fluid reservoir 110 may vary. In some examples, the volumetric capacity of the fluid reservoir 110 may be 3 to 150 cubic centimeters. In some examples, the fluid reservoir 110 is constructed from the same material as the inflatable member 150. In other examples, the fluid reservoir 110 is constructed from a different material than the inflatable member 150. In some examples, the fluid reservoir 110 contains a larger volume of fluid than the inflatable member 150.

In the illustrated embodiment, implantable inflatable device 100 includes a filter 120. In some embodiments, the filter 120 is configured to allow fluid of the device 100 to be passed through it and is configured to prevent larger particles of material that may be within the fluid to pass through the filter 120. For example, in some embodiments, it may be desirable to prevent larger particles from getting into or next to a pump or a valve of the pump assembly 130. Such particles may cause damage to or prevent the pump or valve from operating properly.

The filter 120 may be located at a variety of locations within the device 100 and some embodiments may include more than one filter 120. In some embodiments, the filter 120 is located within the pump assembly 130. In some embodiments, the filter 120 is located between the pump assembly 130 and the fluid reservoir 110. For example, the filter 120 may be located within the connection member 170. In other embodiments, the filter 120 is located between the pump assembly and the inflatable member 150. For example, the filter 120 may be located within the connection member 190.

In the illustrated embodiment, the pump assembly 130 includes a coupling or anchoring member 160. The coupling or anchoring member 160 may be coupled to and extend from a housing of the pump assembly 130. The coupling or anchoring member 160 is configured to facilitate the anchoring or coupling of the pump assembly 130 within the body of the patient.

Figure 2:
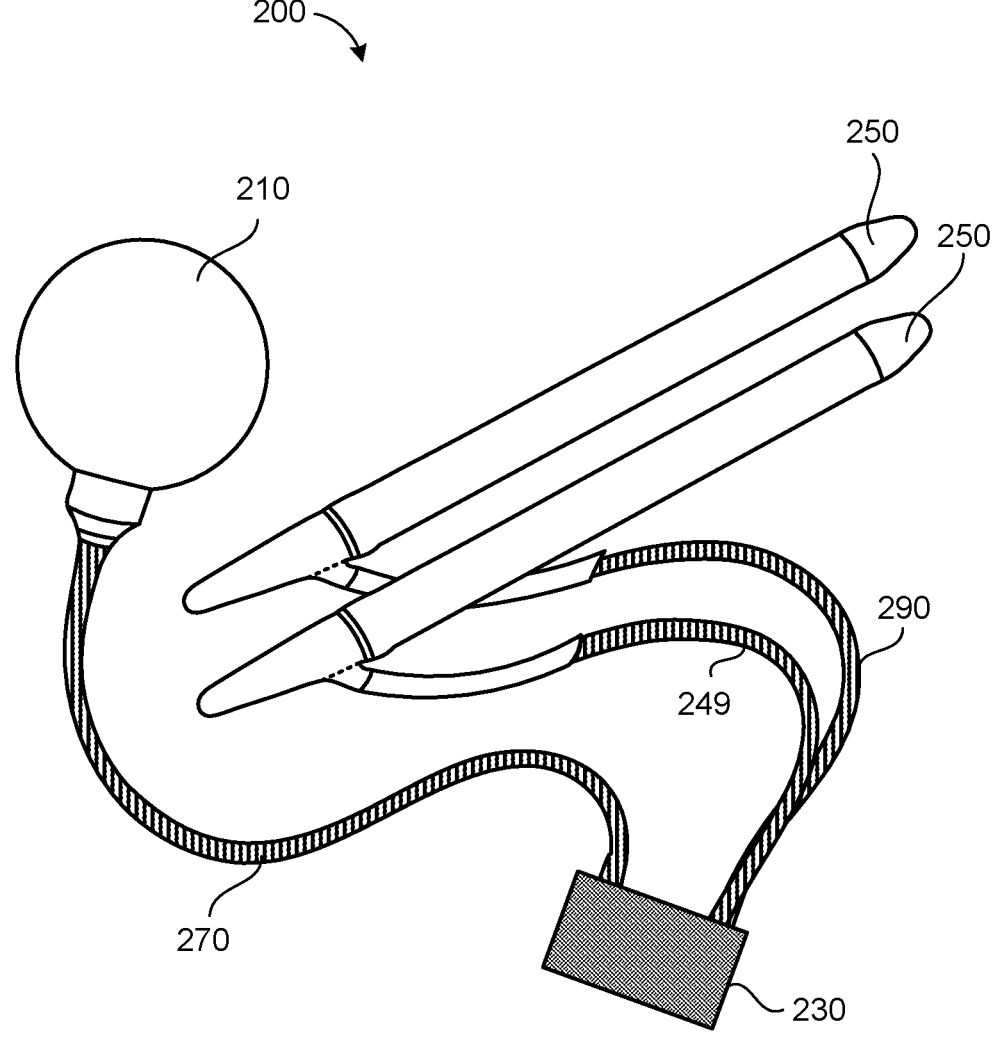
FIG. 2 is a perspective view of an implantable inflatable device according to an aspect.

FIG. 2 illustrates an inflatable penile prosthesis 200 having a pump assembly 230 according to an aspect. The pump assembly 230 may include valves and may include manually actuated pump bulb or may include an electronically controlled pump. The penile prosthesis 200 may include one or more inflatable members or inflatable cylinders 250. In the illustrated embodiment, the prosthesis 200 includes a pair of inflatable cylinders 250. The inflatable cylinders 250 are configured to be implanted in a penis. For example, one of the inflatable cylinders 250 may be disposed on one side of the penis, and the other inflatable cylinder 250 may be disposed on the other side of the penis. Each inflatable cylinder 250 may include a first end portion, a cavity or inflation chamber, and a second end portion having a rear tip. The first end portion of the inflatable cylinder 250 may be at least partially disposed within the crown portion of the penis. The second end portion may be implanted into the patient's pubic region with the rear tip proximate the pubic bone.

The pump assembly 230 may be implanted into the body of the patient. In some embodiments, the pump assembly 230 may be implanted into an abdomen of the patient. A pair of conduit connectors 290 may attach the pump assembly 230 to the inflatable cylinders 250 such that the pump assembly 230 is in fluid communication with the inflatable cylinders 250. Also, the pump assembly 230 may be in fluid communication with a fluid reservoir 210 via a connection member or a conduit connector 270. The fluid reservoir 210 may be implanted into the user's abdomen.

In order to implant the inflatable cylinders 250, the surgeon first prepares the patient. The surgeon often makes an incision in the penoscrotal region, e.g., where the base of the penis meets with the top of the scrotum. In other instances, the surgeon may make an incision in a different location. From the penoscrotal incision, the surgeon may dilate the patient's corpus cavernosae to prepare the patient to receive the inflatable cylinders 250. The corpus cavernosum is one of two parallel columns of erectile tissue forming the dorsal part of the body of the penis, e.g., two slender columns that extend substantially the length of the penis. The surgeon will also dilate two regions of the pubic area to prepare the patient to receive the second end portion. The surgeon may measure the length of the corpora cavernosae from the incision and the dilated region of the pubic area to determine an appropriate size of the inflatable cylinders 250 to implant.

After the patient is prepared, the penile prosthesis 200 is implanted into the patient. The tip of the first end portion of each inflatable cylinder 250 may be attached to a suture. The other end of the suture may be attached to a needle member (e.g., Keith needle). The needle member is inserted into the incision and into the dilated corpus cavernosum. The needle member is then forced through the crown of the penis. The surgeon tugs on the suture to pull the inflatable cylinder 250 into the corpus cavernosum. This is done for each inflatable cylinder 250 of the pair. Once the inflation chamber is in place, the surgeon may remove the suture from the tip. The surgeon then inserts the second end portion. The surgeon inserts the rear end of the inflatable cylinder 250 into the incision and forces the second end portion toward the pubic bone until each inflatable cylinder 250 is in place.

In some embodiment, the pump assembly 230 includes an electric pump or pump system. An example electric pump systems is illustrated in FIG. 3.

In other embodiments, the pump assembly 230 is a manual pump. In such embodiments, a pump bulb of the pump assembly 230 may be squeezed or depressed by the user in order to facilitate the transfer of fluid from the fluid reservoir 210 to the inflatable cylinders 250. For example, in the inflation mode, while the user is operating the pump bulb, the pump bulb may receive the fluid from the fluid reservoir 210, and then output the fluid to the inflatable cylinders 250. When the user switches to the deflation mode, at least some of the fluid can automatically be transferred back to the fluid reservoir 210 (due to the difference in pressure from the inflatable cylinders 250 to the fluid reservoir 210). Then, the user may squeeze the inflatable cylinders 250 to facilitate the further transfer of fluid through the pump assembly 230 to the fluid reservoir 210.

Figure 3:
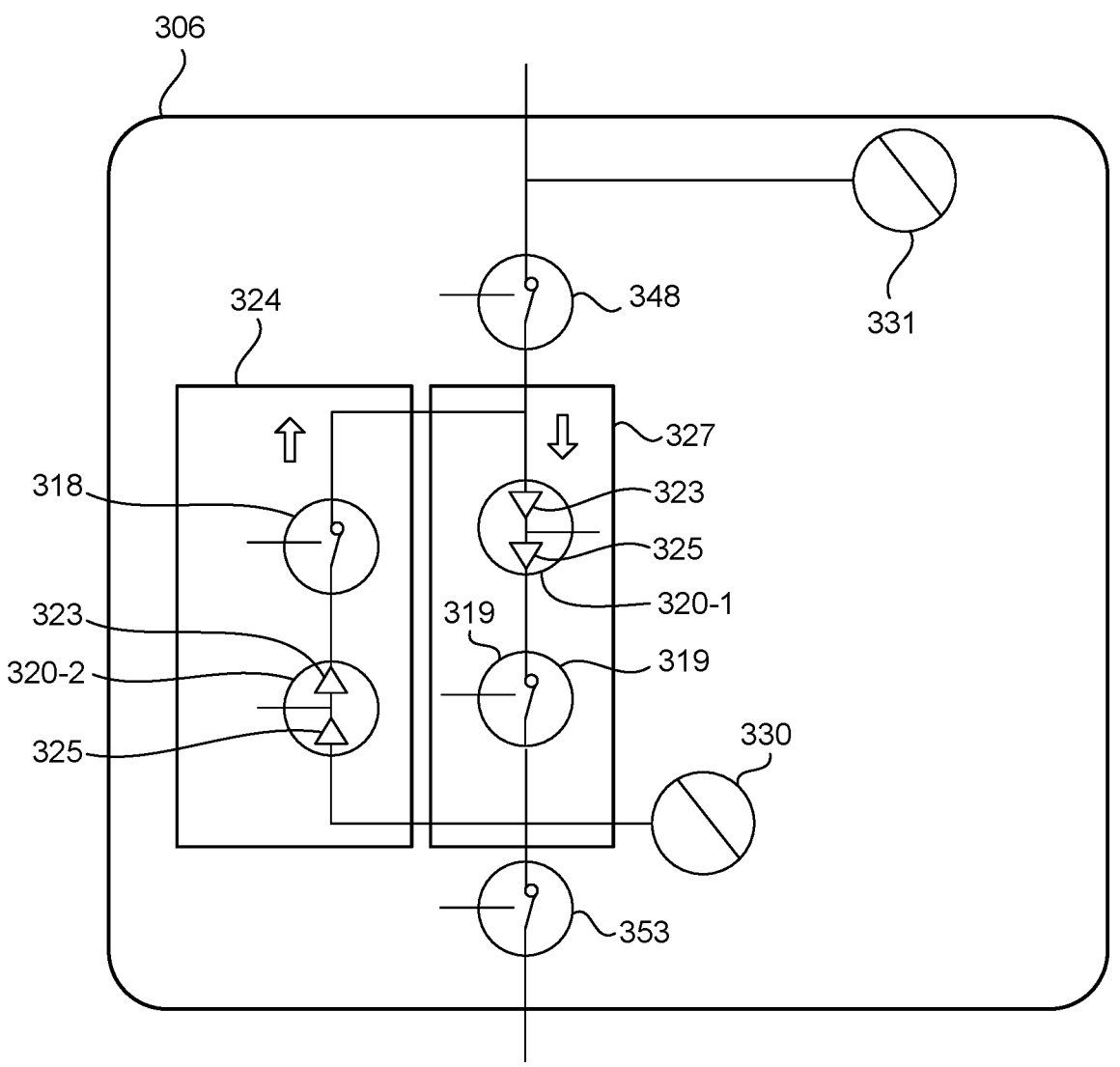
FIG. 3 is a schematic illustration of a pump assembly of the implantable inflatable device of FIG. 2.

FIG. 3 illustrates an example of a portion of an electronic pump assembly 306 according to an aspect. The electronic pump assembly 306 may be an example of the electronic pump assembly 130 of FIG. 1 and/or the electronic pump assembly 230 of FIG. 2 and may include any of the details discussed with reference to the device 100 of FIG. 1 and/or the device 200 of FIG. 2.

The electronic pump assembly 306 is configured to transfer fluid between the fluid reservoir and the inflatable member. The electronic pump assembly 306 may automatically transfer fluid between the fluid reservoir and the inflatable member without the user manually operating a pump (e.g., squeezing and releasing a pump bulb).

The electronic pump assembly 306 includes a pump 320-1 disposed within a fluid passageway 324 (e.g., a fill passageway), and an active valve 318 disposed within a fluid passageway 327 (e.g., an empty passageway). The pump 320-1 may be an electromagnetic pump or a Piezoelectric pump. The pump 320-1 may include a passive check valve 323 and a passive check valve 325. The fluid passageway 327 may be a fluid branch that is separate (and parallel) to the fluid passageway 324. The fluid passageway 327 is the passageway that transfers fluid from the fluid reservoir to the inflatable member. The fluid passageway 324 is the passageway that transfers fluid from the inflatable member to the fluid reservoir. The pump 320-1 is disposed in parallel with the active valve 318.

In some examples, the electronic pump assembly 306 may include an active valve 319 in series with the pump 320-1 (e.g., the pump 320-1 and the active valve 319 are disposed within the fluid passageway 327). In some examples, the electronic pump assembly 306 may include a pump 320-2 in series with the active valve 318 (e.g., the pump 320-2 and the active valve 318 are disposed in the fluid passageway 324). The pump 320-2 may be an electromagnetic pump or a Piezoelectric pump. The pump 320-2 may include a passive check valve 323 and a passive check valve 325. In some examples, the electronic pump assembly 306 includes an active valve 348 that is fluidly connected to the fluid reservoir. The active valve 348 may be in series with either the active valve 318 (and the pump 320-2) or the pump 320-1 (and the active valve 319). In some examples, the electronic pump assembly 306 includes an active valve 352 that is fluidly connected to the inflatable member. The active valve 352 may be in series with either the active valve 319 (and the pump 320-1) or the pump 320-2 (and the active valve 318).

The active valve 348, the pump 320-1, the active valve 318, the active valve 352, the active valve 318, and the pump 320-2 may be electronically controlled by a controller and/or driver. The pump 320-1 and the pump 320-2 may be unidirectional or bidirectional. With respect to the fluid passageway 327, in some examples, the pump 320-1 and the active valve 319 may swap positions (e.g., where the active valve 319 is in series between the active valve 348 and the pump 320-1). With respect to the fluid passageway 324, in some examples, the active valve 318 and the pump 320-2 may swap positions (e.g., where the pump 320-1 is in series with and between the active valve 318 and the active valve 348).

In some examples, one or more additional active valves and/or one or more additional pumps are disposed in series within the fluid passageway 327. In some examples, one or more additional active valves and/or one or more additional pumps are disposed in series within the fluid passageway 324. In some examples, the electronic pump assembly 306 may include one or more additional (and parallel) fluid passageways, where each additional (and parallel) fluid passageway may include one or more active valves and one or more pumps.

In some examples, the electronic pump assembly 306 may include a pressure sensor 330 and a pressure sensor 331. The pressure sensor 330 and the pressure sensor 331 are connected to a controller, where the controller receives the measured pressure from the pressure sensor 330 and the pressure sensor 331.

The pressure sensor 330 is configured to measure the pressure in the inflatable member. In some examples, the pressure sensor is between the valve 352 and the inflatable member. The controller may receive the measured pressure from the pressure sensor 330 and automatically control the active valves and/or the pump to regulate the pressure. In some examples, the pressure sensor 331 is configured to measure the pressure in the fluid reservoir. In some examples, the pressure sensor 331 may detect intra-abdominal pressure (which can increase during activities such as exercise, and the controller can control the active valves and pump to minimize or prevent accidental inflations. In some examples, the electronic pump assembly 306 may include one or more pressure sensors at other locations within the electronic pump assembly 306. For example, a pressure sensor may be disposed between the active valve 348 and the pump 320-1. In some examples, a pressure sensor may be disposed between the pump 320-1 and the active valve 319. In some examples, a pressure sensor may be disposed between the active valve 348 and the active valve 318. In some examples, a pressure sensor may be disposed between the active valve 318 and the pump 320-2.

Figure 4:
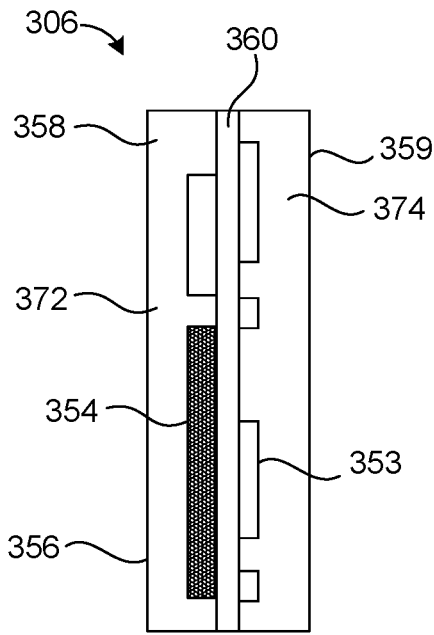
FIG. 4 is see-through view of the pump assembly of the implantable inflatable device of FIG. 3.
Figure 5:
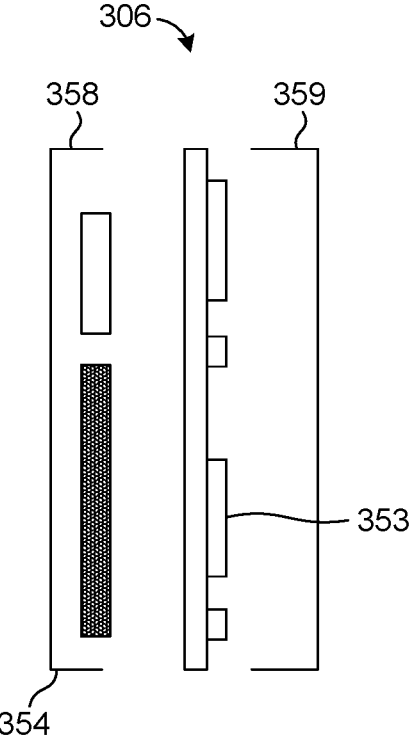
FIG. 5 is an exploded side view of the pump assembly of the implantable inflatable device of FIG. 3.
Figure 6:
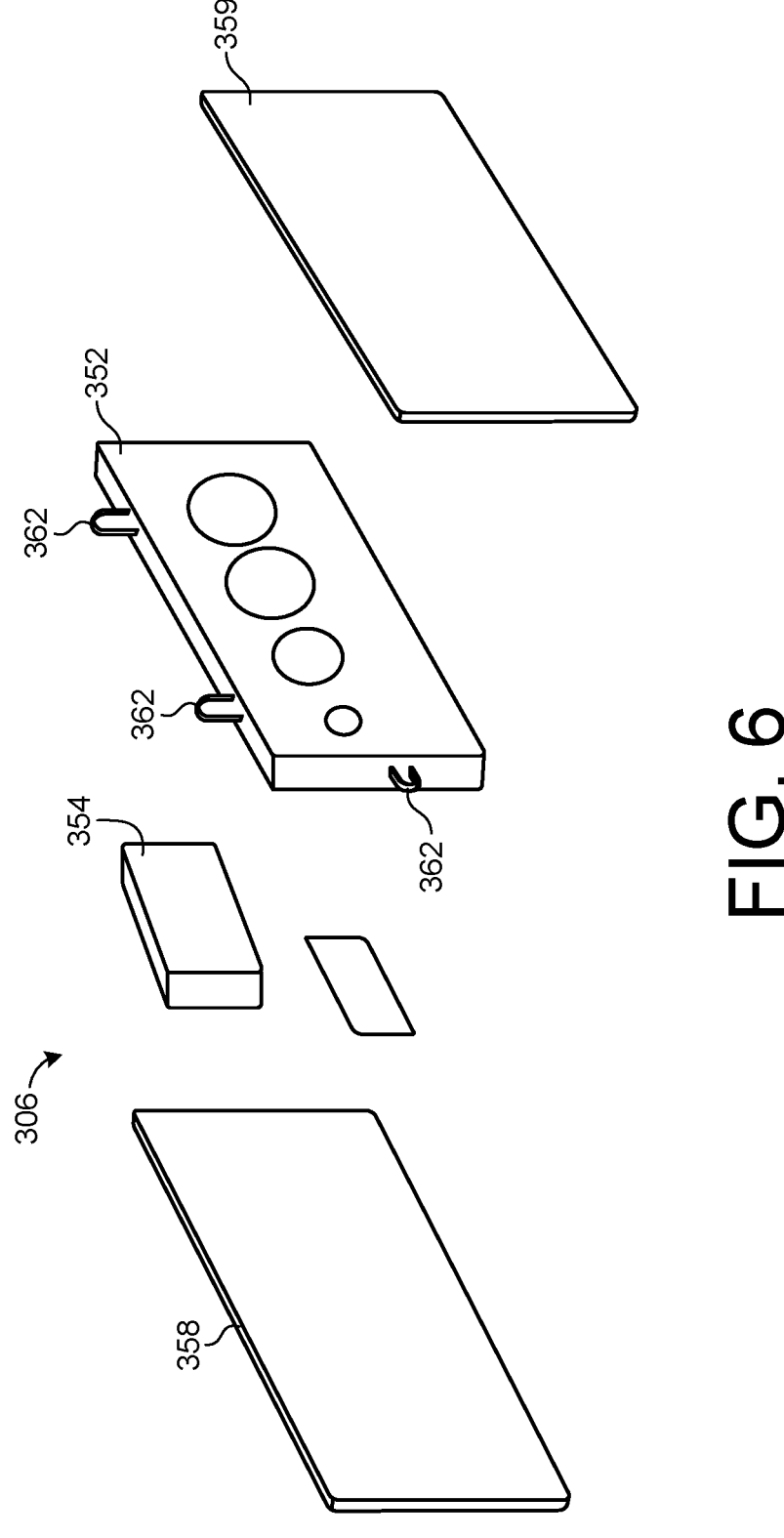
FIG. 6 is an exploded perspective view of the pump assembly of the implantable inflatable device of FIG. 3.

FIG. 4 is see-through view of the pump assembly of the implantable inflatable device of FIG. 3. FIG. 5 is an exploded side view of the pump assembly of the implantable inflatable device of FIG. 3. FIG. 6 is an exploded perspective view of the pump assembly of the implantable inflatable device of FIG. 3.

The pump assembly 306 includes a manifold plate 353, a battery 354, and a housing 356. The housing 356 includes a first portion 358 and a second portion 359. The first portion 358 is configured to be coupled to the manifold plate 353. The second portion 359 is configured to be coupled to the opposite side of the manifold plate 353. Accordingly, two hermetic chambers are formed. Specifically chamber 372 and chamber 374 are formed and are individually sealed. Accordingly, there is no transfer or diffusion of fluid or material between the two chambers 372 and 374 in the case of a failure of the system.

In the illustrated embodiment, the pump assembly 306 includes connection members 362. The connection members 362 are configured to facilitate the coupling or anchoring of the pump assembly 306 within the body of the patient. The connection members 362 form a loop or opening and extend from the housing 356. Accordingly, the connection members 362 may be sutured or otherwise coupled to the bodily tissue of the patient.

Figure 7:
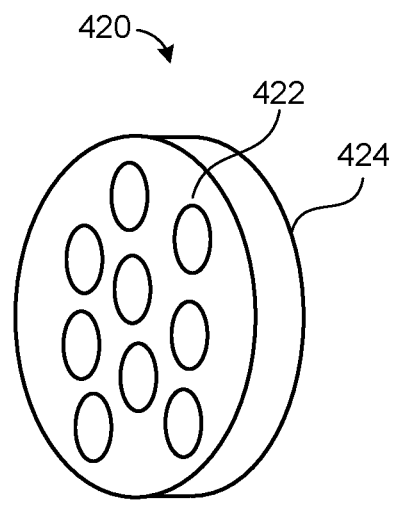
FIG. 7 is a perspective view of the filter of the implantable inflatable device of FIG. 2.
Figure 8:
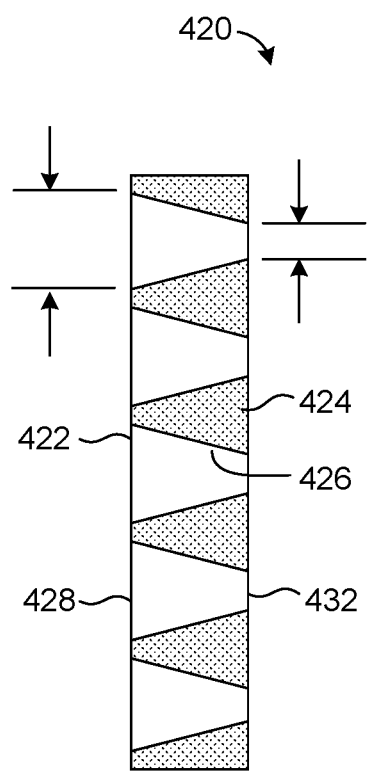
FIG. 8 is a cross-sectional view of the filter of FIG. 7.

FIG. 7 is a perspective view of a filter 420. FIG. 8 is a cross-sectional view of the filter 420. The filter 420 is configured to be disposed within an inflatable implant such as that of FIG. 1 or 2. The filter 420 is configured to allow the fluid of the system to pass through it and is configured to not allow larger particles disposed within the fluid to pass through it. Accordingly, the filter may be positioned to help prevent particles from entering the pump or valves of the pump assembly. In some embodiments, the filter 420 helps prevent pressure spikes within the system.

In the illustrated embodiment, the filter 420 includes a first side 422 and a second side 424 opposite the first side 422. The filter 420 is configured to allow fluid to pass through the filter 420 from one side of the filter to the other side of the filter. In the illustrated embodiment, the filter 420 defines a fluid pathway or passage 426 from the first side 422 to the second side 424. In the illustrated embodiment, the first side 422 of the filter defines an opening 428. The opening 428 has a size, such as a diameter or open area. The second side 424 of the filter 420 defines a second opening 432. The second opening 432 has a size, such as a diameter or open area. The size of the second opening 432 is smaller than the size of the first opening 428. The lumen or pathway 426 extends from the first opening 428 to the second opening 432. Accordingly, the lumen or pathway is tapered.

In some embodiments, the filter 420 is configured to be oriented such that the first side 422 is located towards the pump or pump assembly. In other words, the filter 420 is disposed within the device such that the first side 422 is disposed between the second side 424 and the pump or pump assembly. In other embodiments, the filter may be oriented such that the second side 424 is located towards the pump or pump assembly.

In some embodiments, the filter 420 is disposed within the pump assembly. In other embodiments, the filter 420 is disposed within a connection member such as a tubular member that connects the pump assembly to other portions of the device. For example, in some embodiments, the filter 420 is disposed within a connection member that extends between the fluid reservoir and the pump assembly. In other embodiments, the filter 420 is disposed within a connection member that extends between the pump assembly and the inflatable member.

In some embodiments, the filter 420 is configured to collect or trap particles at or near the second side 424 or the opening 432 defined by the second side 424. For example, in some embodiments, the filter 420 is configured to trap particles within a smaller portion of the lumen or passageway.

In some embodiments, the filter 420 is self-cleaning. For example, in some embodiments, if a particle is trapped or stuck within the lumen at a smaller spot or portion of the lumen, the pressure from the fluid flowing the from the larger portion of the lumen will force the particle out of the filter 420. Additionally, in some embodiments, if a particle is trapped or suck at an opening of the filter, the flow of the fluid would move or remove the particle from being trapped or stuck near the opening.

The filter 420 may be made from a variety of materials. For example, in some embodiments, the filter is made from titanium, stainless steel, ceramic, or a polymetric material. In some embodiments, the material may provide additional features or functions of the filter. For example, in some embodiments, the filter or portions of the filter may be hydrophilic or hydrophobic. In some embodiments, the filter is made using a molding or sintering process. In other embodiments, the filter is formed using a printed or machining method. In other embodiments, the filter is formed using an electrospinning process or method.

Figure 9:
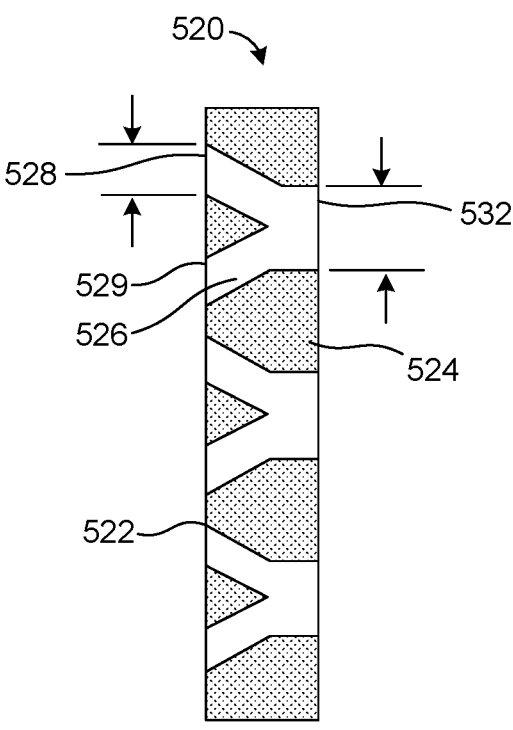
FIG. 9 is a cross-sectional view of a filter according to another aspect.

FIG. 9 is a cross-sectional view of a filter 520 according to an embodiment. The filter 520 is configured to be disposed within an inflatable implant such as that of FIG. 1 or 2. The filter 520 is configured to allow the fluid of the system to pass through it and is configured to not allow larger particles disposed within the fluid to pass through it. Accordingly, the filter may be positioned to help prevent particles from entering the pump or valves of the pump assembly. In some embodiments, the filter 520 helps prevent pressure spikes within the system.

In the illustrated embodiment, the filter 520 includes a first side 522 and a second side 524 opposite the first side 522. The filter 520 is configured to allow fluid to pass through the filter 520 from one side of the filter to the other side of the filter. In the illustrated embodiment, the filter 520 defines a plurality of fluid pathways or passages 526 from the first side 522 to the second side 524. In the illustrated embodiment, the first side 522 of the filter defines openings 528 and 529. The openings 528 and 529 each have a size, such as a diameter or open area. The second side 524 of the filter 520 defines an opening 532. The opening 532 has a size, such as a diameter or open area. The size of the opening 532 is larger than the size of the openings 528 and 529. The lumen or pathway 526 forms a Y shape (or forms separate branches) and extends from the openings 528 and 529 to the opening 532. Accordingly, and as illustrated, in some embodiments, the first side 522 of the filter 520 defines more openings than the second side 524 of the filter 520. In such embodiments, the fluid pathways converge from the first side 522 to the second side 524 and diverge from the second side 524 to the first side 522. In some embodiments, two openings defined by the first side are fluidically coupled to a single opening defined by the second side. In other embodiments, more than two openings defined by the first side are fluidically coupled to a single opening defined by the second side.

Figure 10:
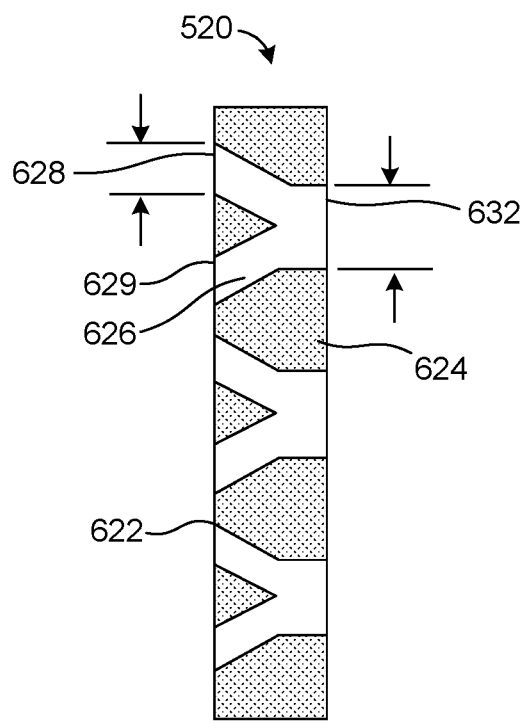
FIG. 10 is a cross-sectional view of a filter according to another aspect.

FIG. 10 is a cross-sectional view of a filter 620 according to an embodiment. The filter 620 is configured to be disposed within an inflatable implant such as that of FIG. 1 or 2. The filter 620 is configured to allow the fluid of the system to pass through it and is configured to not allow larger particles disposed within the fluid to pass through it. Accordingly, the filter may be positioned to help prevent particles from entering the pump or valves of the pump assembly. In some embodiments, the filter 620 helps prevent pressure spikes within the system.

In the illustrated embodiment, the filter 620 includes a first side 622 and a second side 624 opposite the first side 622. The filter 620 is configured to allow fluid to pass through the filter 620 from one side of the filter to the other side of the filter. In the illustrated embodiment, the filter 620 defines a plurality of fluid pathways or passages 626 from the first side 622 to the second side 624. In the illustrated embodiment, the first side 622 of the filter defines openings 628 and 629. The openings 628 and 629 each have a size, such as a diameter or open area. The second side 624 of the filter 620 defines an opening 632. The opening 632 has a size, such as a diameter or open area. The size of the opening 632 is larger than the size of the openings 628 and 629. The lumen or pathway 626 forms a Y shape (or forms separate branches) and extends from the openings 628 and 629 to the opening 632.

In the illustrated embodiment, the size of the opening 628 is larger than the size of the opening 629. In some embodiments, the portion of the lumen or pathway 626 that leads to opening 628 can be used for laminar flow and the portion of the lumen or pathway 626 that leads to opening 629 can be used for turbulent flow.

Figure 11:
FIG. 11 is a perspective view of a filter according to another aspect.
Figure 12:
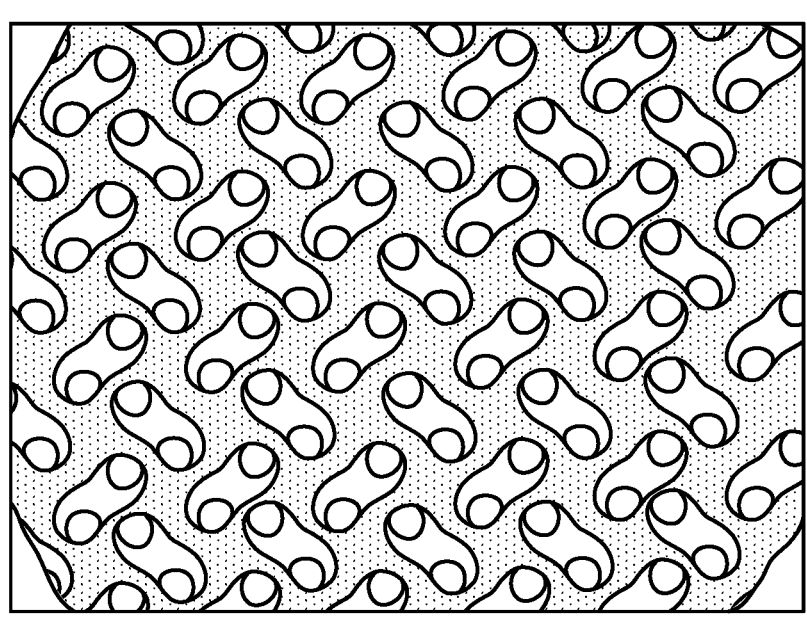
FIG. 12 is a top view of the filter of FIG. 11.

FIG. 11 is a perspective view of a filter 720 according to an embodiment. FIG. 12 is a top view of the filter 720. The filter 720 is configured to be disposed within an inflatable implant such as that of FIG. 1 or 2. The filter 720 is configured to allow the fluid of the system to pass through it and is configured to not allow larger particles disposed within the fluid to pass through it. Accordingly, the filter may be positioned to help prevent particles from entering the pump or valves of the pump assembly. In some embodiments, the filter 620 helps prevent pressure spikes within the system.

In some embodiments, the filter 720 defines fluid pathways that are non-linear, curved, or torturous. In some embodiments, the particles are trapped within the curved pathways capture or trap the particles. In some embodiments, the filter 720 is a lattice filter. In the illustrated embodiment, the filter 720 is a gyroid filter, such as a walled gyroid. In some embodiments, the filter 720 is formed using an electrospinning method or process.

While certain features of the described implementations have been illustrated as described herein, many modifications, substitutions, changes, and equivalents will now occur to those skilled in the art. It is, therefore, to be understood that the appended claims are intended to cover all such modifications and changes as fall within the scope of the embodiments.

What is claimed is:

1. An implantable inflatable device, comprising:
a fluid reservoir defining a cavity;
an inflatable member;
a pump assembly configured to transfer fluid from the fluid reservoir to the inflatable member; and
a filter member, the fluid being configured to pass through the filter member when the pump assembly transfers the fluid between the fluid reservoir to the inflatable member, the filter member defining a first opening, a second opening, a third opening, and a fluid pathway fluidically coupling the first opening, the second opening, and the third opening.

2. The inflatable device of claim 1, wherein the pump assembly includes a pump, the filter member is operatively coupled between the pump and the fluid reservoir.

3. The inflatable device of claim 1, wherein the pump assembly includes a pump, the filter member is operatively coupled between the pump and the inflatable member.

4. The inflatable device of claim 1, further comprising:
a connection member extending between the fluid reservoir and the pump assembly to operatively couple the fluid reservoir to the pump assembly, the filter member being disposed within the connection member.

5. The inflatable device of claim 1, further comprising:
a connection member extending between the inflatable member and the pump assembly to operatively couple the inflatable member to the pump assembly, the filter member being disposed within the connection member.

6. The inflatable device of claim 1, wherein the filter member is a self-cleaning filter.

7. The inflatable device of claim 1, wherein the filter member defines a fluid pathway, the fluid pathway having a tapered shape.

8. The inflatable device of claim 1, wherein the first opening has a size, the second opening has a size, the third opening has a size, the size of the first opening being different than the size of the second opening and being different than the size of the third opening.

9. The inflatable device of claim 1, wherein the first opening is disposed on the first side of the filter, the second opening is disposed on the second side of the filter, the third opening is disposed on the second side of the filter.

10. The inflatable device of claim 1, wherein the filter member is a lattice filter.

11. The inflatable device of claim 1, wherein the filter member defines a fluid pathway, the fluid pathway having a torturous path.

12. The inflatable device of claim 1, wherein the filter member is disposed within the pump assembly.

13. The inflatable device of claim 1, wherein the pump assembly includes a housing, the housing having anchoring members.

14. An implantable inflatable device, comprising:
a fluid reservoir defining a cavity;
an inflatable member;
a pump assembly configured to transfer fluid from the fluid reservoir to the inflatable member;
a first connection member extending between the fluid reservoir and the pump assembly;
a second connection member extending between the inflatable member and the pump assembly; and
a filter member, the filter member defines a first opening, a second opening, and a lumen extending between the first opening and the second opening, the first opening having a size, the second opening having a size, the size of the first opening being larger than the size of the second opening.

15. The inflatable device of claim 14, wherein the filter member is disposed within the first connection member.

16. The inflatable device of claim 14, wherein the filter member is disposed within the second connection member.

17. The inflatable device of claim 14, wherein the filter member is a self-cleaning filter.

18. The inflatable device of claim 14, wherein the filter member defines a fluid pathway, the fluid pathway having a tapered shape.

\* \* \* \* \*